(12) United States Patent
Lee et al.

(10) Patent No.: US 9,308,172 B2
(45) Date of Patent: Apr. 12, 2016

(54) DEVICE AND METHOD FOR ENCAPSULATION OF HYDROPHILIC MATERIALS

(71) Applicant: Board of Trustees of Michigan State University, East Lansing, MI (US)

(72) Inventors: Ilsoon Lee, Okemos, MI (US); Shaowen Ji, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 72 days.

(21) Appl. No.: 14/062,236

(22) Filed: Oct. 24, 2013

(65) Prior Publication Data
US 2014/0120169 A1     May 1, 2014

Related U.S. Application Data

(60) Provisional application No. 61/718,870, filed on Oct. 26, 2012.

(51) Int. Cl.
*A61K 9/16* (2006.01)
*A61K 31/711* (2006.01)
*A61K 31/7105* (2006.01)

(52) U.S. Cl.
CPC ............. *A61K 9/1647* (2013.01); *A61K 9/1694* (2013.01); *A61K 31/711* (2013.01); *A61K 31/7105* (2013.01)

(58) Field of Classification Search
None
See application file for complete search history.

(56) References Cited

U.S. PATENT DOCUMENTS

| 5,902,591 | A * | 5/1999 | Herstein | A61K 8/26 424/401 |
| 6,777,002 | B1 * | 8/2004 | Vuaridel | A61K 9/1647 424/489 |
| 2004/0115277 | A1 * | 6/2004 | Kissel et al. | 424/489 |
| 2004/0175429 | A1 * | 9/2004 | Alavattam et al. | 424/490 |
| 2008/0299200 | A1 * | 12/2008 | Leser | B01F 17/0028 424/484 |
| 2009/0311295 | A1 * | 12/2009 | Mathiowitz | A61K 8/11 424/401 |

OTHER PUBLICATIONS

Lathrop, D. et al., "Turbulent Flow between Concentric Rotating Cylinders at Large Reynolds Number," Physical Review Letters, vol. 68, No. 10, published Mar. 9, 1992, p. 1515-1518.*
Villanova, J. et al., "Pharmaceutical acrylic beads obtained by suspension polymerization containing cellulose nanowhiskers as excipient for drug delivery," European Journal of Pharmaceutical Sciences 42, published online Jan. 15, 2011, p. 406-415.*
J. M. Morais et al., "W/O/W Multiple Emulsions Obtained by One-Step Emulsification Method and Evaluation of the Involved Variables," Journal of Dispersion Science and Technology, 29: 63-69, 2008.*
H.Y. Kwon et al., "Preparation of PLGA nanoparticles containing estrogen by emulsification-diffusion method," Colloids and Surfaces A: Physicochemical and Engineering Aspects, 182 (2001) 123-130.*
E. Dluska et al., "One-step preparation method of multiple emulsions entrapping reactive agent in the liquid-liquid Couette-Taylor flow," Chemical engineering and Processing 48 (2009) 438-445.*
A. Pawlik et al., "Encapsulation stability of dulex emulsions prepared with SPG cross-flow membrane, SPG rotating membrane and rotor-stator techniques—A comparison," Journal of Membrane Science 415-416 (2012) 459-468.*
Shaowen Ji, et al; "Transitional behavior of polymeric hollow microsphere formation in turbulent shear flow by emulsion diffusion method"; Article Polymer #53 (2012) pp. 205-212; Nov. 16, 2011.
Wasfy M. Obeidat; "Recent Patents Review in Microencapsulation of Pharmaceuticals Using the Emulsion Solvent Removal Methods"; Paper in Recent Patents on Drug Delivery & Formulation, 2009, vol. 3, No. 3, pp. 178-192; Revised Jun. 29, 2009.

* cited by examiner

*Primary Examiner* — Tracy Vivlemore
*Assistant Examiner* — Minica Shin
(74) *Attorney, Agent, or Firm* — Harness, Dickey & Pierce, P.L.C.

(57) ABSTRACT

A process for preparing polymeric composite particles includes the steps of preparing an oil phase containing a biodegradable polymer and a water phase containing a hydrophilic compound or nanoparticle and emulsifying the oil phase in the water phase to form emulsions. Then solvent is removed from the emulsions to prepare the particles in the form of capsules and spheres in sizes from 0.01 μm (10 nm) to 50 μm.

26 Claims, 5 Drawing Sheets

DEVICE AND METHOD FOR ENCAPSULATION OF HYDROPHILIC MATERIALS

CROSS-REFERENCE TO RELATED APPLICATIONS

This application claims the benefit of U.S. Provisional Application No. 61/718,870 filed on Oct. 26, 2012, the full disclosure of which is hereby incorporated by reference.

FIELD

The present invention relates to a method for encapsulating hydrophilic as well as hydrophobic drugs and entities within polymeric nano/microspheres or hollow microspheres.

INTRODUCTION

Encapsulation process has been widely applied in pharmaceutical and biomedical industry, food systems, printing, cosmetics, and agricultural area. In drug delivery system, encapsulating for controlled release can protect drugs from degradation, improve the bioavailability of drugs, minimize drug side effects, reduce dosing frequency, and mask drug taste and odor. Due to the world wide interest, improvement for efficient encapsulation becomes an area of great importance to extend its applications and meet diverse needs.

One promising method of encapsulation is an emulsion solvent removal technique, which can provide a versatile incorporation of hydrophilic or hydrophobic compounds. Unlike spray drying, the solvent removal technique can be used for highly temperature-sensitive compounds. And unlike the coacervation method, solvent removal leaves no phase separation-inducing agents behind in the final products as coacervation method.

Polymeric systems with suitable biodegradability and biocompatibility are widely employed as carriers for active compounds. As the polymers are gradually degraded into non-toxic small molecules and adsorbed in vivo, the active compound is gradually released. In the production of polymeric particles by encapsulation processes, poly(lactic acid) (PLA) is the most commonly used by far owing to its excellent biocompatibility. PLA has been studied as a controlled release carrier for various drugs since 1970s (Suong-Hyu Hyon, Seiyaku Kojo (Pharmaceutical Factory), Vol. 13, No. 10, p 552, 1983).

Many types of hydrophobic compounds have been formulated into PLA using the solvent removal technique. A hydrophobic compound or drug is firstly dispersed or dissolved in an organic solvent in which PLA is also dissolved. The organic phase which is usually called dispersed phase is then emulsified into an aqueous phase called continuous phase to form the oil-in-water (O/W) emulsion droplets. The solvent in the emulsion is diffused into the continuous phase and droplets are hardened to solid particles loaded with the targeted compound. However, this method is applicable only to hydrophobic compounds since hydrophilic ones may not be dissolved in the organic solvent. Many alternative methods have been attempted to incorporate hydrophilic compounds. In the W/O/W double emulsion method disclosed in Japanese Patent Publication (Kokai) No. 100516/1985, hydrophilic compounds are encapsulated into an aqueous solution, which is emulsified with organic solvent to form the W/O emulsion droplets. These are further dispersed into a second aqueous solution to obtain W/O/W double emulsions. However, this method requires tedious preparation procedures, rigid control of temperature and viscosity. It also introduces the third components into the final products.

Other techniques have focused on preparing polymeric microspheres from emulsions by solvent removal to encapsulate hydrophilic compounds (for example Hyon et al. U.S. Pat. No. 5,100,669). However, the presence of residual organic solvent in the final particles is a drawback in terms of safety and the environment.

There remains a need to develop methods of encapsulating hydrophilic materials and compounds that avoid the noted drawbacks.

SUMMARY

Biodegradable polymeric composite particles and a process for preparation thereof are provided. The biodegradable polymeric composites are loaded with hydrophilic compounds or hydrophilic nanoparticles (NPs). A process for preparing the polymeric composite particles includes the steps of preparing an oil phase containing the biodegradable polymer and a water phase containing the hydrophilic compounds or nanoparticles, emulsifying the oil phase in the water phase to form emulsions, and removing the solvent from emulsions to harden the polymeric composites. In various embodiments, the process provides for solvent removal from emulsions to prepare the polymeric composite particles, which are in the form of capsules and spheres in sizes from 0.01 μm (10 nm) to 50 μm.

BRIEF DESCRIPTION OF THE DRAWINGS

The drawings described herein are for illustrative purposes only of selected embodiments and not all possible implementations, and are not intended to limit the scope of the present disclosure.

DESCRIPTION

Figure 1:
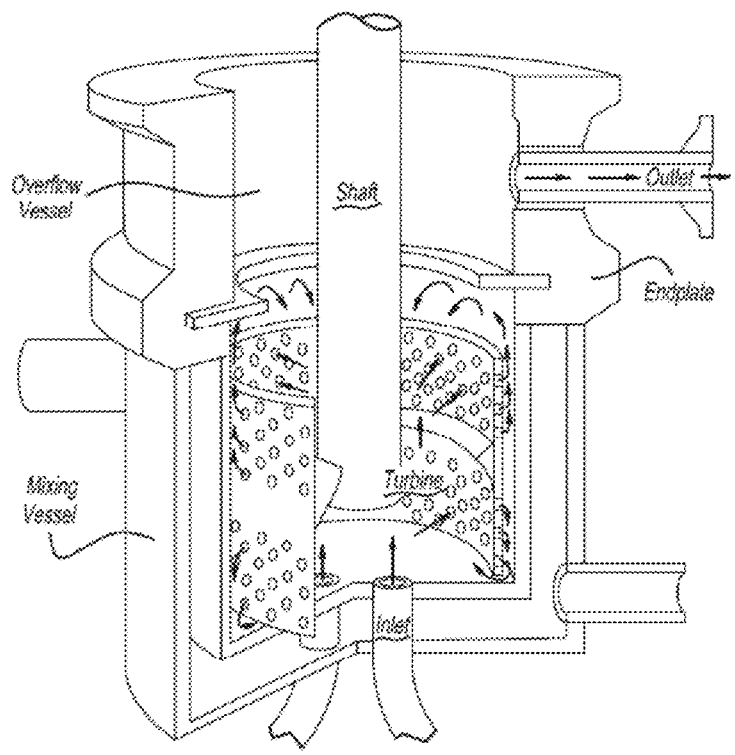
FIG. 1 is a schematic of the modified Taylor-Couette nanomixer geometry.

The terms "oil phase" and "organic phase" are used interchangeably. Likewise, the second phase with which the oil or organic phase is emulsified is equally referred to as the "water phase" or the "aqueous phase." When one phase is dispersed in another as droplets, the droplet phase is called the dispersed phase and the other phase is the continuous phase.

Unless context requires otherwise, solvent refers to an organic solvent other than the water or the aqueous phase. A water immiscible solvent is one in which water is not miscible. A water immiscible solvent can be slightly soluble in water or sparingly soluble, but the solubility does not extend to all proportions as it would for a water miscible solvent. Similarly, by "hydrophilic material, "hydrophilic compound," and similar terms, it is meant a material or compound that dissolves more readily (i.e. to a higher extent) in water than in the water immiscible solvent.

In one embodiment, a method of encapsulating a water soluble active ingredient in a polymer composite is provided. The polymeric composite contains a hydrophobic biodegradable polymer as well as the water soluble active ingredient. The method involves the steps of 1) preparing an organic phase comprising the biodegradable polymer and a solvent; 2) preparing a water phase comprising the active ingredient, water, and a surfactant; 3) combining the organic phase and the water phase in a single step under emulsification conditions that form a W/O/W emulsion; and 4) removing the solvent from the W/O/W emulsion to harden the polymeric composites. The solvent is not miscible in water, and the active material is more highly soluble in water than in the solvent. The viscosity of the combined phases is controlled by incorporating suitable levels of thickeners (described below) into the water phase.

In another embodiment, a one-step emulsification process is provided for incorporating hydrophilic materials into a hydrophobic matrix, such as containing a biodegradable polymer. In similar fashion to the embodiment described in the above paragraph, the method involves the steps of 1) mixing an organic phase and a water phase in a mixer to form an emulsion wherein the water phase is the continuous phase; 2) removing solvent from the emulsion to form particles comprising a polymeric composite, in a continuous aqueous phase; and 3) collecting the particles by physical separation from the continuous phase. Here, the mixer used is outfitted with concentric cylinders, one of which rotates relative to the other to provide mixing. Further, the viscosity of the combined phases and the speed of the mixer are selected to bring the mixing into the viscous turbulent regime. The organic phase contains a biodegradable polymer and a solvent not miscible with water and the water phase comprises the hydrophilic material and a surfactant. The viscosity of the combined phases is controlled by incorporating suitable levels of thickeners (described below) into the water phase.

In another embodiment, a method of making a nanocomposite comprising cellulose nanowhiskers or cellulose microfibrils and a biodegradable polymer selected from poly (L-lactic acid), poly(D,L-lactic acid), poly(glycolic acid), poly(lactide-co-glycolide) involves a similar process of emulsification. The method involves encapsulating the nanowhiskers or microfibrils in the biodegradable polymer using a one-step emulsion process comprising:

preparing an organic phase comprising the biodegradable polymer and a solvent;
preparing a water phase comprising the nanowhiskers or microfibrils, water, and a surfactant;
combining the organic phase and the water phase in a single step under emulsification conditions that form a W/O/W emulsion; and
removing the solvent from the W/O/W emulsion, wherein the solvent is not miscible in water.

These and other embodiments are described herein with respect to various examples of hydrophilic material, solvent, thickener, biodegradable polymer, emulsification conditions, nanoparticles, and so on. It is to be understood that examples of one aspect or limitation can be combined with others to provide useful emulsification processes described herein. Non-limiting description of various aspects of the invention are also provided in the working examples by way of illustration.

In one aspect, it has been discovered that by manipulating the operation conditions, such as emulsification temperature and viscosity of water phase, a single emulsion process can produce not only O/W type emulsion but also an in-situ W/O/W type emulsion within seconds. The multiple emulsion droplets are then used to encapsulate hydrophilic compounds in the inner water phase. In the single emulsion method, a biodegradable polymer is dissolved in a water-immiscible organic solvent as the oil phase and a hydrophilic compound is dissolved in the surfactant containing water as the water phase. The oil phase is then emulsified once into the water phase to give the W/O/W emulsion droplets. Afterward, solvent is removed from the oil phase of the resulting emulsions by diffusion or evaporation to form the polymeric composite particles. The formation of said in-situ or dynamic W/O/W emulsion droplets in seconds from single emulsion method enables the incorporation of hydrophilic compounds inside of the oil-polymer shell in a very short time, for example within seconds.

Although the invention is not to be limited by theory, in one aspect the formation of W/O/W emulsion droplets can be thought of as kinetically controlled process wherein under proper conditions described herein the W/O/W droplets form spontaneously in a short time, even if other emulsion structures would be more thermodynamically stable. In this aspect, the one step method relies on mixing for a long enough period of time to form the W/O/W droplets (which has been observed to be quite short, being generally a matter of seconds), but not so long as to reach the more thermodynamically favored condition wherein the hydrophilic material simply cannot be encapsulated into the hydrophobic polymer.

The one-step and fast process can be applied to encapsulate hydrophilic compounds or nanoparticles in composites along hydrophobic polymer components such as the noted biodegradable polymers. In various embodiments, the hydrophilic materials are selected from active materials that do not readily dissolve in water-immiscible organic solvents, but are more readily soluble in water or in an aqueous phase. These include pharmaceuticals, peptides or proteins, nucleic acids, and nanoparticles with size less than 100 nm. In various embodiments, the hydrophilic materials are selected from active materials or other material useful in food systems, printing, cosmetics, and the agricultural area. In the pharmaceutical area, the methods can be used to prepare compositions containing a hydrophilic active pharmaceutical ingredient (API). Such pharmaceuticals include, for example, antibiotics, hypotensives, antidiabetics, antidepressants, antiallergic agents, hormones, and so on. Peptides or proteins include, for example, nisin, insulin, bacitracin, gastrin, pancreozymin, bovine serum albumin (BSA), ovalbumin (OVA), enzymes, and the like. Nucleic acids include DNA, RNA, and XNA. Nanoparticles include, for example, iron oxide and other hydrophilic nanoparticles (NPs), other composite NPs, and the like. Other hydrophilic nanoparticles such as cellulose nanowhiskers or cellulose microfibrils can also be emulsified by the method. In various embodiments, the method is suitable for hydrophilic molecules and hydrophilic nanoparticles with size less than the thickness of the polymer shell wall (~100 nm). Encapsulations of nisin and of hydrophilic nanoparticles are further exemplified below.

The water immiscible solvents are not soluble in water, are sparingly soluble in water, or are slightly or even considerably soluble in water. Whatever the level of solubility of the solvent in water, it is not complete solubility as would be implied by the term miscible. Non-limiting examples of water-immiscible solvents include ethyl acetate, methylene chloride, chloroform, carbon tetrachloride, dichloroethane, methyl ethyl ketone, and the like. Mixtures of two or more solvents can be used. For emulsion process, any organic solvent that dissolves PLA or other hydrophobic polymers but that is not miscible with water can be used to form suitable emulsions. When it comes to drug delivery, the selections are more limited because the solvent also has to be non-injurious to health.

The biodegradable polymer, which is used as carriers for the composite particles, and which is provided in the organic phase described herein, can be any polymer that is readily decomposed in the human body and that preferably shows little or no biological activities. Examples of the biodegradable polymer include poly(lactic acid), poly(glycolic acid), poly(D,L-lactic acid), poly(lactide-co-glycolide), and carboxylic acid and ester derivatives of them. Further examples include poly(hydroxybutyric acid), poly(caprolactone), poly(valerolactone), polyanhydrides, poly(acrylic acid), poly(m-ethylmethacrylate), or their copolymers thereof, like poly(lactide-co-glycolide), or a mixture thereof. The biodegradable polymers can be used alone or in a combination or mixture of two or more.

Surfactants are included in the water phase. Suitable surfactants are those having a hydrophile-lipophile-balance (HLB) in a range favoring formation of O/W emulsions, which is normally a value on higher side. They can be selected from nonionic, cationic, or anionic surfactants. Examples include polyvinyl alcohol (PVA), carboxylic acid salt surfactants (straight chain fatty acids, coconut fatty acids, N-acylated sarcosine, N-acylated bile acids), ethoxylated surfactants like polysorbate 80 and polyoxyethylene-polyoxypropylene block surfactants such as those exemplified by the Pluronic® F68 of the examples.

Viscosity enhancers, also called thickeners, are also used. When present, they can be incorporated into the oil phase or the water phase, their function being to adjust the viscosity to a range where emulsion proceeds in a viscous turbulent regime and under conditions where preferred W/O/W emulsions are formed upon mixing. Glycerol is a preferred thickener for its suitability as a safe ingredient for human ingestion. Non-limiting examples of soluble thickeners include natural gums (such as acacia, tragacanth, alginic acid, carrageenan, locust bean gum, guar gum, gelatin), cellulose derivatives (such as sodium carboxymethylcellulose, methyl cellulose, hydroxyethyl cellulose, hydroxypropyl methyl cellulose), sugars (such as glucose, fructose), polymers (e.g. polyvinyl alcohol, polyvinyl pyrrolidone), and clays (bentonite).

The process of making the polymer composites involves solvent removal from the W/O/W emulsion to harden the particles. While mixing the phases under emulsification conditions is a key step to form O/W or W/O/W emulsions which determine the size and shape of final particles. The step of solvent removal removes the organic solvent from oil droplets and solidifies the polymer as particles. In one embodiment, solvent removal is carried out by adding the emulsion to an excess of water to provide a diffusion process or a solvent diffusion process. Other removal methods, such as evaporation and freeze drying, can also be applied for this purpose. But diffusion is usually a mild and simple process and is preferred in some embodiments for that reason. During diffusion for solvent removal, mild stirring or agitation is preferably applied to achieve good mass transfer between two phases.

When the water and oil phases are being combined with mixing, the water phase is normally used in sufficient excess so as to favor the formation of emulsions in which the water phase is the continuous phase. In various non-limiting examples discussed herein, the water to oil phase are provided in a ratio of 3 water to 1 oil by volume. If the ratio goes too low, there would be a tendency to form emulsions where the oil phase is continuous, which is undesirable.

The oil phase contains a solvent and the water phase contains water. Upon mixing of the two phases, intimate contact will result in mass transfer between the phases leading to equilibrating the solvent and the water. In various embodiments, the water phase before mixing is formulated to contain some of the solvent, and even to be saturated in the solvent. Likewise in some embodiments it is preferred to provide the oil phase as one saturated in water. Generally, it is preferred to saturate the oil and water phases in this way before emulsification, because the two phases are preferably immiscible with each other. Carrying out the emulsification with saturated oil and water phases provides further advantages by lowering likelihood of bursting or collapsing emulsion droplets during a subsequent step of diffusion to remove solvent.

The emulsification process can be carried out by a conventional method, for example, by stirrer, turbine impeller emulsifier, ultrasonic dispersion mixer, homogenizer, high-pressure emulsifier, and the like. In a preferred embodiment, a Taylor-Couette type mixer is used, such as the T K Filmics nanomixer (Model 40-40) from the PRIMIX Corporation, Japan. Emulsion conditions are chosen to prepare a W/O/W emulsion from the oil phase and water phase blended in a one-step emulsification process. Conditions are readily achieved in the preferred mixer at speeds of 10-50 m/sec. Generally, the shear rate is chosen to be on the high side, for example above 1000 $sec^{-1}$, above 2000 $sec^{-1}$, above 3000 $sec^{-1}$, above 4000 $sec^{-1}$, above 5000 $sec^{-1}$, above 7500 $sec^{-1}$, above 10,000 $sec^{-1}$, and above 12,000 $sec^{-1}$. It is about 12,500 $sec^{-1}$ in an exemplary embodiment. As noted above, the thickener is used among reasons to adjust the viscosity so that the system achieves turbulent flow during emulsification. In various embodiments, the Reynolds number, which is a dimensionless parameter and a function of viscosity among other variables, is 4000 or greater during emulsification, indicating turbulent flow, is 2300-4000, indicating a transient flow state between laminar and turbulent, or is above 2300, indicating that the flow is not formally considered as laminar. Though not limited by theory, it is believed that some turbulence of mixing tends to help reach the emulsification conditions required for formation of the desired emulsion structure.

In a preferred embodiment, dynamic encapsulation is accomplished by operating in the turbulent viscous regime during the emulsification process.

The emulsification process is also affected by the temperature at which the process is carried out. Temperature affects the viscosity and polymer properties and is important for that reason. In addition, it is generally preferred to run the emulsification mixing at a temperature above the glass transition temperature of the biodegradable polymer.

The formation of a W/O/W emulsion can be followed and confirmed using the visualization techniques such as those using water soluble dyes described in the working examples.

After solvent removal by diffusion or other process, the final particles are separated from the water phase by physical means such as centrifugation or filtration, in non-limiting examples. After a preferred washing step, the obtained particles can be further treated such as by drying in air or an inert gas, or by or lyophilization or other techniques.

Advantageously, the mixer provides thorough mixing to form W/O/W emulsions from one-step emulsification in a very short time, for example in 60 seconds or less in batch mode when the size of the batch and the capacity of the mixer are matched. The process can be scaled up for use in larger mixers. In addition to batch mode, the process can be carried out continuously, with care taken to provide a suitable residence time comparable to that found to be advantageous in the batch procedure. In various embodiments, the mixture of water and oil phases is subjected to emulsification conditions for 120 seconds or less. In general, lower residence times lead to faster turnover and improved process efficiency. In a preferred embodiment, the phases to be emulsified are subject to a shear rate of above 1000 $sec^{-1}$, above 2000 $sec^{-1}$, above 3000 $sec^{-1}$, above 4000 $sec^{-1}$, above 5000 $sec^{-1}$, above 7500 $sec^{-1}$, above 10,000 $sec^{-1}$, and above 12,000 $sec^{-1}$ for a minimum time of at least 5 seconds, at least 10 seconds, at least 30 seconds, at least 60 seconds, or at least 120 seconds. Advantageously, emulsification is accomplished in 10 minutes or less, in 5 minutes or less, in 120 seconds or less, in 90 seconds or less, in 60 seconds or less, in 45 seconds or less, in 30 seconds or less, in 20 seconds or less, or in 10 seconds or less.

EXAMPLES

Example 1

Figure 9:
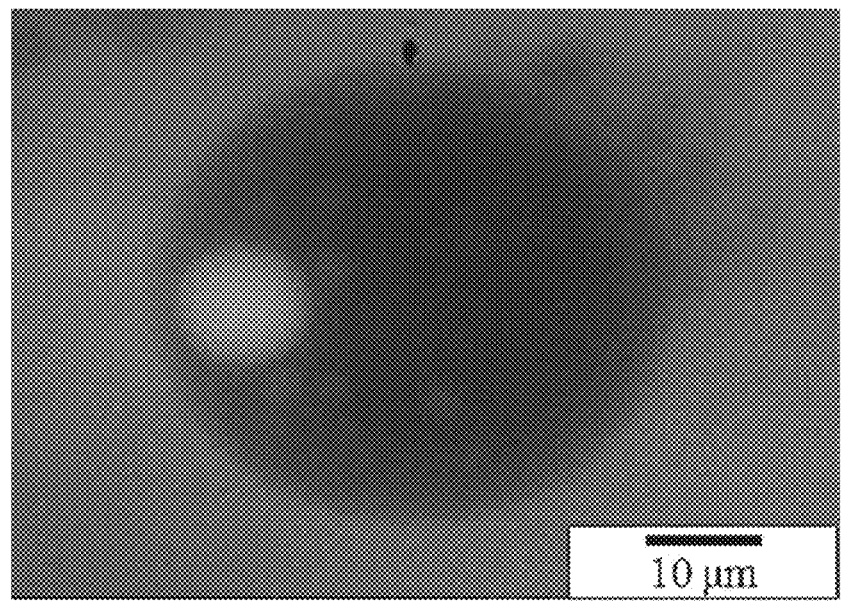
FIG. 9 shows a sample of the emulsion solution.

To follow and confirm the presence and formation of W/O/W emulsions in the one step method, conventional methods can be used. In one method, water soluble dye is applied into the emulsion, where it preferentially goes into the aqueous phase, enabling visualization. After emulsification and before the solvent removal, one drop of emulsion solution is taken onto a glass slide and observed under a microscope. The colored dye is observed in the aqueous part of the emulsion. The colored dye is shown as the lighter color in FIG. 9. Droplets-in-drop structure (W/O/W) instead of O/W structure was found in the solution which is similar to multiple emulsion drops. (Light Gray color represents the water phase; Dark Gray color represents the oil phase).

Example 2

2.1 Materials

Nisin Z powder was provided by Metna Corporation (activity >38,000 IU/mg). Poly(D,L-lactic acid) (PLA, $M_w$=51,000 Da, $T_g$=52.5° C.) was purchased from LakeShore Biomaterials (California, USA). The poloxamer Pluronic F68 (PF68) (average $M_w$=8,400 Da) was obtained from Sigma Aldrich. It is a low foaming and non-ionic surfactant consisting of block polymers in which central polyoxypropylene oxide (PPO) flanked by two polyoxyethylene oxide (PEO) tails. Ethyl acetate (EtOAc) and glycerol were from J. T. BAKER and used as received. All the chemicals used were analytical grade without further purification. All aqueous solutions in the processes were prepared with deionized (DI) water supplied by a Barnstead nanopure Diamond-UV purification unit equipped with a UV source and final 0.2 μm filter at 18.2 MΩ purity.

2.2 PLA/Nisin Particles Production

EtOAc and water were used as dispersed organic solvent (oil phase) and dispersion aqueous medium (water phase), respectively. They were mutually saturated to avoid any surface irregularities of droplets by sudden inter-diffusion during emulsification. PLA solutions were prepared by dissolving PLA into 6 mL water-saturated EtOAc (O). 18 mL EtOAc-saturated aqueous solution (W) was added with PF68 and then mixed with different volume fractions of glycerol to adjust its viscosity. Nisin powders were added into the aqueous solution to reach different concentrations. Well-mixed aqueous solutions were centrifuged at 12,000 rpm for 10 min to remove the insoluble materials before emulsification. A modified high shear Taylor-Couette type T K Filmics nanomixer (Model 40-40) from the PRIMIX Corporation, Japan was used for experiments to generate the uniform emulsion samples. Both oil phase and water phase solutions were added in the chamber of nanomixer. The oil phase solution was emulsified with the aqueous continuous solution at the mixing speed rate of 12,500 $s^{-1}$ and temperature of 60° C. in 1 min to give the water-in-oil-in-water emulsion (W/O/W). The W/O/W emulsion was then added to plenty of pure DI water and stirred in a beaker to induce the diffusion of EtOAc from oil phase. After overnight diffusion, the colloidal dispersion was thus transferred to glass vial and stored at 4° C. for future use.

2.3 Nisin Encapsulation Quantification

Reverse-phase HPLC was applied to quantify the nisin concentration in the solutions. The amount of the encapsulated nisin in the final particles was determined by the change of nisin amount in the solution before and after the emulsion diffusion process.

2.4 Zeta Potential Analysis for Particle Surface Charge

Zeta potential was measured using 90Plus Brookhaven Instrument. PLA particles were added to 1 mM KCl solution. Zeta potential measured is an average of 10 runs for each sample. The results are shown as means±standard deviation.

2.5 Particle Morphology Characterization

Colloidal dispersion after dialysis was dropped on a glass slide and placed on a model FluoView confocal laser scanning microscope (CLSM). Images were made at 633 nm for confocal reflection and at 405/430-470 nm (ex./em.) for autofluorescence at two channels.

Scanning Electron Microscope (SEM) was used to estimate the mean particle size as well as coefficient of variation for particle size. SEM used for high resolution imaging was JEOL 6400 at Center for Advanced Microscopy in Michigan State University, at working distance of 8 mm and accelerating voltage of 6 KV. PLA particles were collected onto 0.1 μm filter membrane and washed by plenty of pure DI water under vacuum. Dried particles along with membrane were then covered with gold coating facilitating their conductivity under electron microscope.

2.6 Results and Discussions

FIG. 1 shows a scheme of chamber geometry and principle of nanomixer. It consists of concentric cylinder pair with inner turbine rotating at peripheral speeds from 0 to 40 m/s which can generate high shear stress on the processing materials and achieve extremely high Reynolds number (Re). Mixing or reaction is carried out under an open system which is also used as an injection port. The emulsification is carried out in the Couette-Taylor flow which occurs in the annular space between those two cylinders. Shear stress can be generated by either laminar flow or turbulent flow depending on Re. Based on the definition of Re for fluids and the type of forces mainly responsible for drop breakup, the most important regimes in turbulent flow are turbulent viscous and turbulent inertial. When the process fluid is spinning at the same speed as the turbine, it is pressed strongly against the inside of vessel wall. The perforated cylinder wheel with many holes in the circumferential wall allows the whirling process fluid to spurt out through the holes due to the centrifugal force. The process fluid is divided into two flows along the inside wall. The upward flow smashes against the top and is going downward, while the downward flow smashes against the bottom and is going upward. These two flows return to the inside of the spinning thin film with numerous small turbulent eddies. Then the process is repeated within the nanomixer. The processing temperature of emulsification can be controlled by flowing heating or cooling fluid around the mixing chamber.

Figure 2:
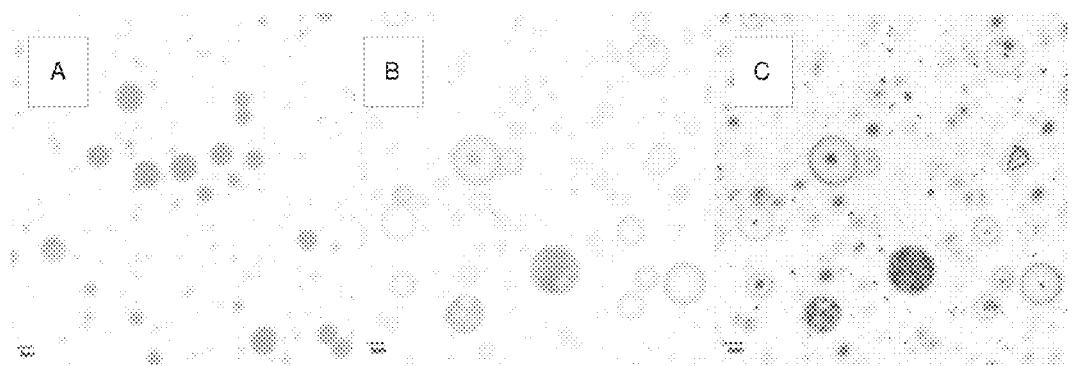
FIG. 2A is the nisin distribution on the outer surface of the final particles.
FIG. 2B is the nisin distribution within the particles when applying z-series imaging.
FIG. 2C is the nisin distribution inside the particles mostly overlapped with the region which represents the shell wall of hollow polymeric microspheres.

Confocal scanning laser microscopy (CLSM) can be used to directly observe the distribution of nisin in the particles. In FIG. 2, the gray region correlates with peptides and proteins which is nisin used in the system, and the black/dark gray region correlates with the PLA. FIG. 2A shows the nisin distribution on the outer surface of final particles. When applied z-series imaging, the nisin distribution within the particles could be observed (FIG. 2B). The darker regions in FIG. 2C showing the nisin distribution inside the particles mostly overlapped with the region that represents the shell wall of hollow polymeric microspheres, indicating the successful encapsulation of nisin not only on the surface of polymeric composite particles but also within their shell walls.

Figure 3:
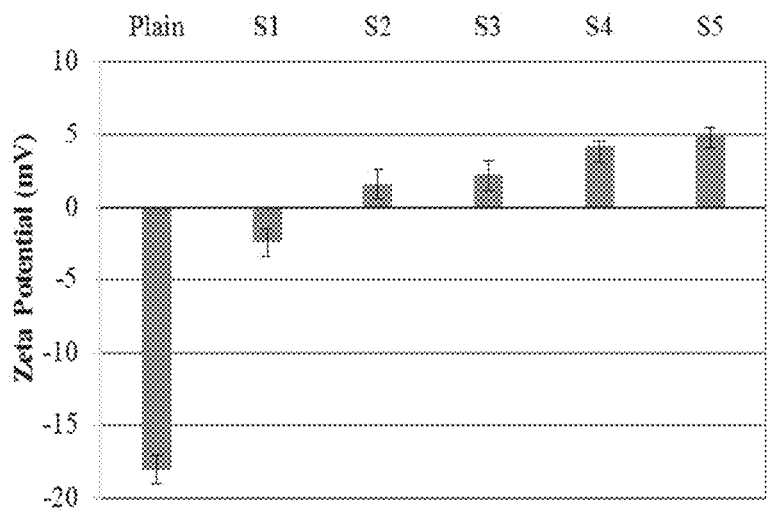
FIG. 3 shows the surface charges of plain PLA particle and polymeric composite particles with nisin loadings of 0.025 (S1), 0.075 (S2), 0.125 (S3), 0.175 (S4), and 0.225 (S5) mg/ml in the water phase solution.
Figure 4:
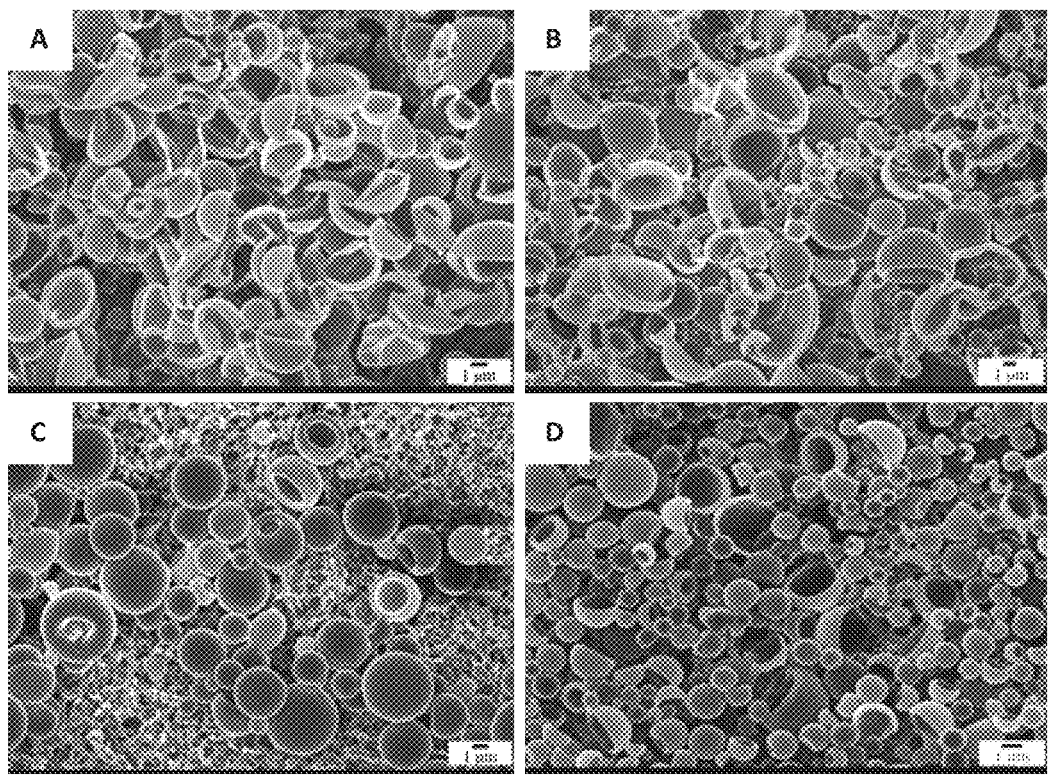
FIG. 4 is SEM images of final polymeric composite particles with nisin loadings of 0.05 (A), 0.25 (B), 0.5 (C), 0.75 (D) mg/ml in the water phase solution.

Zeta potential analysis was performed to measure the surface charge of final particles prepared at different nisin loadings. FIG. 3 shows the surface charges of plain PLA particle and polymeric composite particles with nisin loadings of 0.025 (S1), 0.075 (S2), 0.125 (S3), 0.175 (S4), and 0.225 (S5) mg/ml in the water phase solution. Plain PLA particles have been well known to present negative charges on the surface. This is consistent with the zeta potential measured as −18 mV. And nisin is known to be a cationic peptide. The polymeric composite particles showed slightly positive charged properties on the surface which indicated that the negative surface charge of PLA particles was shielded in the presence of nisin. The surface charge increased with increasing nisin loadings confirming that there was nisin adsorbed on the surface of PLA carriers. FIG. 4 shows SEM images of final polymeric composite particles with nisin loadings of 0.05 (A), 0.25 (B), 0.5 (C), 0.75 (D) mg/ml in the water phase solution. We can see that increasing nisin concentration in the water phase has little effect on the particle size and shape. The concept of dynamic control of particle production by our emulsion solvent removal technique is still applicable. The thickness of particle shell wall was increased with increasing the nisin loading. Supported by previous data that indicated the existence of nisin in the polymeric composite particles, it may be due to the increase of nisin encapsulated within the polymer carriers that generated the thicker shell wall.

Figure 5:
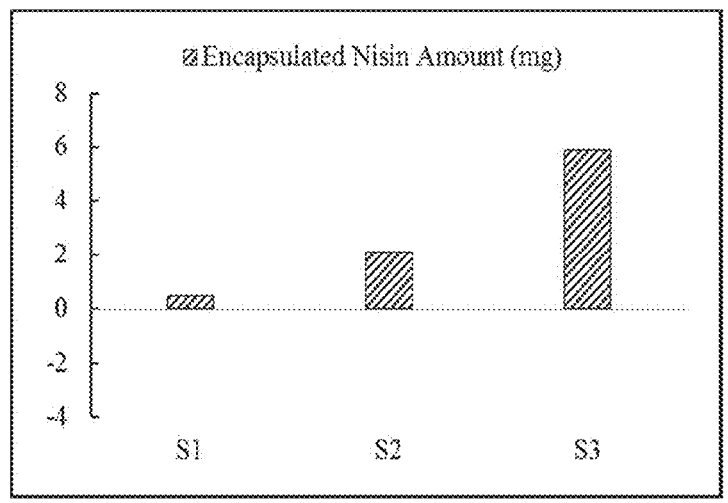
FIG. 5 shows the amount of nisin encapsulated in the polymeric particles increased with increasing the nisin loadings in the water phase solution.

The amount of nisin encapsulated in the polymeric particles is increased with increasing the nisin loadings in the water phase solution (as shown in the FIG. 5; S1, S2, and S3 represent the particles with nisin loadings of 1.5, 2.0, 3.0 mg/ml). This indicates the possibility of controlling the encapsulation amount by adjusting the formulations. Since all the remaining nisin in the aqueous solution can be collected and reused, the waste of nisin after the preparation can be avoided.

Figure 6:
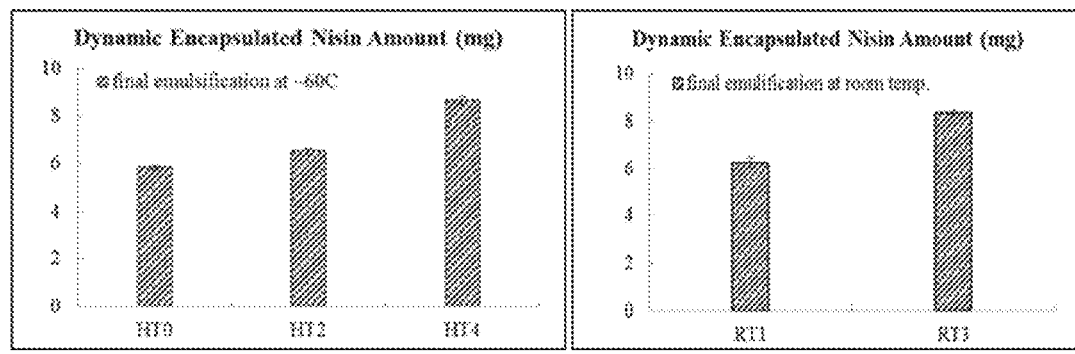
FIG. 6 demonstrates the effect of alternating emulsification temperatures between ~60° C. and room temperature on the encapsulated nisin amount.

The emulsion solvent removal process in our system has been tested as a dynamically reversible control on the particle size and shape, for example solid nanospheres and hollow microspheres, by controlling the key processing parameters. This reversible manipulation can also be used in the encapsulation. FIG. 6 shows the example of the effect of alternating emulsification temperatures between ~60° C. and room temperature (25° C.) on the encapsulated nisin amount. All emulsification processes were firstly ended at the mixing temperature of ~60° C. HT0, HT2, and HT4 represent that the emulsification process was performed by alternating temperatures 0 time, 2 times, and 4 times and the ending emulsification temperatures were at ~60° C. RT1 and RT3 represent that the emulsification was performed by alternating temperatures 1 time and 3 times, and the ending emulsification temperatures were at room temperature. The more alternations of temperatures the emulsification process took, the more nisin amount was encapsulated. Therefore, the encapsulation amount as well as particle size and shape can be easily controlled by this process which shows superior advantages of easy operation and scale-up production.

Example 3

3.1 Materials

The materials are the same as in the Example 1. Hydrophilic iron oxide nanoparticles (magnetite NPs) were prepared as in Liu, Z. L., et al., *Synthesis and characterization of ultra fine well-dispersed magnetic nanoparticles*. Journal of Magnetism and Magnetic Materials, 2004. 283: p. 258.

3.2 PLA/Magnetite NPs Preparation

The same oil and water phase solutions were prepared. Magnetite solution was added into the aqueous solution at the volume ratio of 1 to 50. The same T K Filmics nanomixer (Model 40-40) was used for experiments to generate the uniform emulsion samples. Both oil phase and water phase solutions were added in the chamber of nanomixer. The oil phase solution was emulsified with the aqueous continuous solution at the mixing speed rate of 12,500 $s^{-1}$ and temperature of 60° C. in 1 min to give the oil-in-water emulsion (O/W). The O/W emulsion was then added to plenty of pure DI water and stirred in a beaker to induce the diffusion of EtOAc from oil phase. After overnight diffusion, the colloidal dispersion was thus transferred to glass vial and stored at 4° C. for future use. Prepared particles were firstly collected by the magnet and then washed by water.

3.3 Microscopic Observation

SEM was used to observe the morphological changes of final polymeric composite particles. Part of the colloidal dispersion was placed in a sealed dialysis membrane and gently stirred in the pure DI water at room temperature overnight. PLA particles were purified by allowing diffusion of glycerol and excess PF68 molecules through the selectively permeable membrane. Transmission electron microscopy (TEM) was done on polymeric composite particles using JEOL 2200FS 60 kV field emission TEM. Copper grids coated with carbon were used to support particles. Microtoming was applied to get a thin cross-sectional slice from the final particle sample for microscopic inspection.

3.4 Results and Discussions

Figure 7:
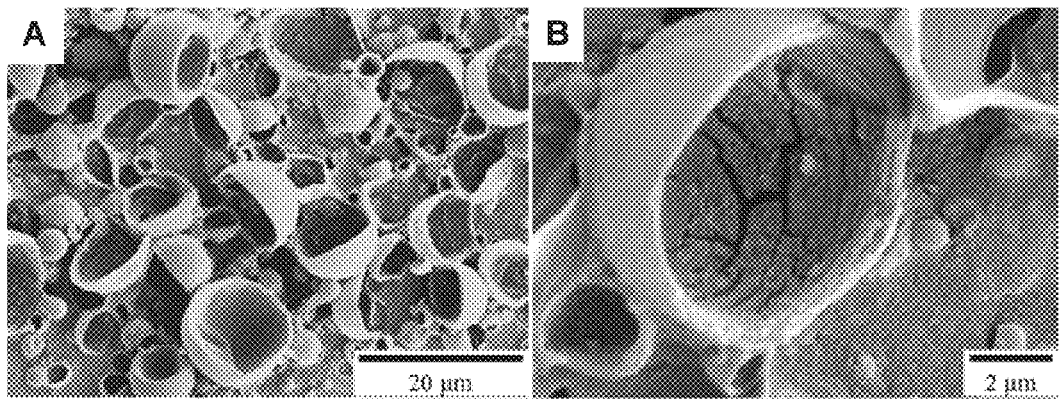
FIG. 7A is an SEM image of the hollow structure of the polymeric composite particles after successful encapsulation of magnetite NPs within polymer carriers.
FIG. 7B is a high SEM magnification image of the surface details of individual particles.

These final particles can be collected by the magnet indicating the successful encapsulation of magnetite NPs within polymer carriers. SEM images have shown that the polymeric composite particles kept the hollow structure which suggests that the manipulation of our emulsion solvent removal technique is still applicable for nanoparticle encapsulation system (FIG. 7A). High SEM magnification revealed the surface details of individual particles. The shell wall turned to be rough and large amount of nanoparticles were found to be adsorbed or embedded on the inner or outer surface of particles (FIG. 7B).

Figure 8:
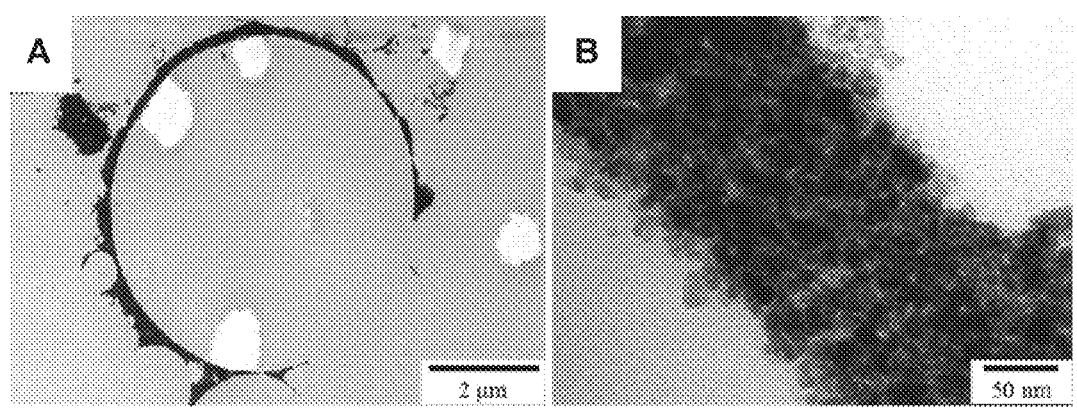
FIG. 8A is an TEM image of the single composite particle.
FIG. 8B is a TEM image at a high magnification on part of the particle shell wall demonstrating a magnetite NPs.

In order to further investigate the distribution of magnetite nanoparticles, TEM was used for observing the sectional view of single composite particle. Consistent with the observation of SEM, hollow structure was clearly seen (FIG. 8A). When high magnification was focused on part of the particle shell wall, magnetite NPs were found greatly cumulated within it (FIG. 8B). This confirms that magnetite NPs have been encapsulated in the composite particles and our process is suitable for encapsulating NPs in certain size range.

What is claimed is:

1. A method of encapsulating a hydrophilic ingredient in nano- or micro-particles comprising a hydrophobic biodegradable polymer to make a polymeric composite, the method comprising:
   preparing an organic phase comprising the biodegradable polymer and a solvent;
   preparing a water phase comprising the hydrophilic ingredient, water, and a surfactant;
   combining the organic phase and the water phase in a single step under emulsification conditions that form a W/O/W emulsion, wherein the emulsification conditions include running at a Reynolds number higher than 2300; and
   removing the solvent from the W/O/W emulsion to harden the polymeric composites, wherein the solvent is not miscible in water, and wherein the ingredient is more highly soluble in water than in the solvent.

2. A method according to claim 1, wherein the organic phase is saturated in water and the water phase is saturated in solvent.

3. A method according to claim 1, wherein the solvent is selected from dichloromethane, methylene chloride, methyl ethyl ketone, ethyl acetate, chloroform, dichloroethane, and carbon tetrachloride.

4. A method according to claim 1, wherein the emulsification conditions include operating at a shear rate of about 12,500 $s^{-1}$.

5. A method according to claim 1, wherein the emulsification conditions include running at a Reynolds number higher than 4000.

6. A method according to claim 1, wherein the emulsification conditions include mixing the organic phase and water phase in a Taylor-Couette mixer.

7. A method according to claim 1, wherein the mixed phases contain an effective amount of a thickener molecule that is soluble in water, wherein the effective amount is sufficient to raise the viscosity to a level where the mixing occurs in a turbulent regime in a modified Taylor-Couette mixer.

8. A method according to claim 1, wherein the hydrophilic ingredient is selected from peptides, proteins, and nucleic acids.

9. A method according to claim 1, wherein the hydrophilic ingredient is selected from RNA and DNA.

10. A method according to claim 1, wherein the hydrophilic ingredient is selected from cellulose nanowhiskers and microfibrils.

11. A method according to claim 1, wherein the hydrophilic ingredient is selected from metallic nanoparticles, organic nanoparticles, and inorganic nanoparticles.

12. A method according to claim 1, wherein the biodegradable polymer is selected from poly(L-lactic acid), poly(D,L-lactic acid), poly(glycolic acid), and poly(lactide-co-glycolide).

13. A method according to claim 1, wherein the solvent is removed by diffusion.

14. A method according to claim 7, wherein the thickener is selected from natural gums, cellulose derivatives, sugars, polymers, and clays.

15. A method of making a nanocomposite comprising cellulose nanowhiskers or cellulose microfibrils and a biodegradable polymer selected from poly(L-lactic acid), poly(D, L-lactic acid), poly(glycolic acid), poly(lactide-co-glycolide), the method comprising encapsulating the nanowhiskers or microfibrils in the biodegradable polymer using a one-step emulsion process comprising:
   preparing an organic phase comprising the biodegradable polymer and a solvent;
   preparing a water phase comprising the nanowhiskers or microfibrils, water, and a surfactant;
   combining the organic phase and the water phase in a single step under emulsification conditions that form a W/O/W emulsion, wherein the emulsification conditions include running at a Reynolds number higher than 2300; and
   removing the solvent from the W/O/W emulsion,
wherein the solvent is not miscible in water.

16. A method according to claim 15, wherein the organic phase is saturated in water and the water phase is saturated in solvent.

17. A method according to claim 15, wherein the solvent is selected from dichloromethane, methylene chloride, methyl ethyl ketone, ethyl acetate, chloroform, dichloroethane, and carbon tetrachloride.

18. A method according to claim 15, wherein the emulsification conditions include operating at a shear rate of about 12,500 $s^{-1}$.

19. A method according to claim 15, wherein the emulsification conditions include running at a Reynolds number higher than 4000.

20. A method according to claim 15, wherein the emulsification conditions include mixing the organic phase and water phase in a Taylor-Couette mixer.

21. A method according to claim 15, wherein the mixed phases contain an effective amount of a thickener molecule that is soluble in water, wherein the effective amount is sufficient to raise the viscosity to a level where the mixing occurs in a turbulent regime in a Taylor-Couette mixer.

22. A method according to claim 14, wherein the thickener is selected from natural gums, acacia, tragacanth, alginic acid, carrageenan, locust bean gum, guar gum, and gelatin.

23. A method according to claim 14, wherein the thickener is selected from cellulose derivatives, sodium carboxymethylcellulose, methyl cellulose, hydroxyethyl cellulose, and hydroxypropyl methyl cellulose.

24. A method according to claim 14, wherein the thickener is selected from sugars, glucose, and fructose.

25. A method according to claim 14, wherein the thickener is selected from polymers, polyvinyl alcohol, and polyvinyl pyrrolidone.

26. A method according to claim 14, wherein the thickener is selected from clays and bentonite.

* * * * *